(12) United States Patent
Bachler

(10) Patent No.: US 8,625,829 B2
(45) Date of Patent: Jan. 7, 2014

(54) PARTIALLY IMPLANTABLE HEARING AID

(75) Inventor: Herbert Bachler, Zurich (CH)

(73) Assignee: Advanced Bionics AG, Staefa (CH)

( * ) Notice: Subject to any disclaimer, the term of this patent is extended or adjusted under 35 U.S.C. 154(b) by 162 days.

(21) Appl. No.: 13/145,502

(22) PCT Filed: Jan. 21, 2009

(86) PCT No.: PCT/EP2009/050674
§ 371 (c)(1),
(2), (4) Date: Jul. 20, 2011

(87) PCT Pub. No.: WO2009/047370
PCT Pub. Date: Apr. 16, 2009

(65) Prior Publication Data
US 2011/0280426 A1    Nov. 17, 2011

(51) Int. Cl.
*H04R 25/00* (2006.01)
(52) U.S. Cl.
USPC ............................ 381/326; 381/322; 381/328
(58) Field of Classification Search
USPC ................. 381/312, 322, 323, 324, 326, 328; 600/25; 607/55, 56, 57; 623/10
See application file for complete search history.

(56) References Cited

U.S. PATENT DOCUMENTS

| 3,764,748 | A | * | 10/1973 | Branch et al. | 607/57 |
| 5,814,095 | A | * | 9/1998 | Muller et al. | 607/57 |
| 7,289,639 | B2 | * | 10/2007 | Abel et al. | 381/312 |
| 2005/0267549 | A1 | | 12/2005 | Della Santina et al. | |
| 2006/0189841 | A1 | * | 8/2006 | Pluvinage | 600/25 |
| 2007/0036375 | A1 | * | 2/2007 | Jensen | 381/312 |

FOREIGN PATENT DOCUMENTS

| WO | WO-03/063542 | 7/2003 |
| WO | WO-2006/045148 | 5/2006 |

OTHER PUBLICATIONS

International Preliminary Report on Patentability received in International Application No. PCT/EP2009/050674 dated Aug. 4, 2011.
International Search Report and Written Opinion received in International Application No. PCT/EP2009/050674 dated May 7, 2009.

* cited by examiner

*Primary Examiner* — Suhan Ni
(74) *Attorney, Agent, or Firm* — ALG Intellectual Property, LLC

(57) ABSTRACT

A partially implantable hearing aid is provided, comprising an external audio signal unit to be worn at least in part in a user's ear canal, an implantable unit and external means for transmitting power transcutaneously to the implantable unit via an inductive link, the external audio signal unit comprising audio signal processing means for producing processed audio signals from input audio signals and means for transmitting the processed audio signals via an optical link through an ear drum to an optical receiver of the implantable unit, the implantable unit comprising an actuator for stimulating the user's hearing, a power receiving means and a driver unit for transforming the received audio signals into an input signal to the actuator.

16 Claims, 2 Drawing Sheets

PARTIALLY IMPLANTABLE HEARING AID

The invention relates to a partially implantable hearing aid.

Fully implantable hearing aids are cosmetically appealing and stigma-free, so that such systems are potentially attractive despite the need for surgery and the relatively high costs involved in such systems. However, presently such fully implantable hearing aids still are not widely applied due to serious technical deficits and disadvantages encountered by the presently available systems. For example, the rechargeable batteries do not last for lifetime and hence must be replaced every couple of years by another surgery. Also, technological progress and new benefits cannot be applied after implantation, so that products get outdated rather fast. Moreover, subcutaneous microphones are rather noisy, both in terms of system noise (reduced sensitivity due to titanium membrane and package) and body noise picked-up by the microphone. The microphone position is mostly on the side of the head as opposed to the ear-canal, so that spatial information which is normally offered by the pinna is lost.

Partially implantable hearing aids, such as all currently available cochlear implants (CI), are cosmetically less appealing, but overcome some of these problems. Usually, the battery and the signal processing unit are assembled into a body worn or head worn device, which is connected via an inductive wireless link with the implanted part of the system. Typically, the external device is worn behind the ear and has a relatively large size, with the largest part of the device being covered by the battery. The reason is that the battery has to last at least one full day and that the wireless transmission of both power and data through one and the same inductive link is very inefficient. Moreover, the total power consumption is dependent on the thickness of the skin.

EP 1 251 809 B1 relates to a partially implantable hearing aid designed as a cochlear implant, wherein the external part of the system comprises a device to be worn in the ear-canal, which device includes the microphone, the audio signal processing unit and a transmitter for transmitting the audio signals via a radio frequency (RF) link to the implanted part. The implanted part comprises a receiver located in the mastoid and the cochlear electrode. The transcutaneous power link is realized by an external charging coil and an implanted coil, with the receiver being used both in the power link and the data link.

A similar system is described in US 2005/0267549 A1, wherein it is mentioned that the external microphone may be located in the ear canal and may be connected via an RF link to the implanted part.

WO 2006/045148 A2 relates to a partially implantable CI-system comprising a BTE (Behind-The-Ear)—like device including the external microphone, the battery and the audio signal processing unit. The audio signals are transmitted via a capacitive data link to the receiver which is implanted in the mastoid and which is also used in the inductive power link.

U.S. Pat. No. 7,289,639 B2 relates to a partially implantable hearing aid comprising an implanted actuator which may be a mechanical actuator coupled to an ossicle or a cochlear electrode, and an external device which is to be worn in the ear canal and which comprises a microphone, a battery, an audio signal processing unit and an optical transmitter which is provided for establishing an optical link through the ear drum to an optical receiver implanted in the middle ear cavity. The optical link also is intended to serve as the power supply for the implanted actuator. A similar device is described in US 2006/0189841 A1.

It is an object of the invention to provide for a partially implantable hearing aid which allows for a cosmetically appealing design by avoiding the need for bulky external parts of the system.

According to the invention, this object is achieved by a partially implantable hearing aid as defined in claim 1.

The invention is beneficial in that, by transmitting the audio signals via an optical link to the implantable unit while power is transmitted via an inductive link to the implantable unit, the power consumption of the system can be reduced, since the power link can be optimized due to its separation from the data link. In addition, by arranging the audio signal processing means and the audio signal transmission means in an external unit to be worn at least in part in the ear canal, the size of the externally visible part of the system can be minimized.

Preferably, the actuator is a cochlear electrode. The external audio signal unit may be designed as a CIC (Completely-In-the-Canal) device. Preferably, the power transmitting means is a charging adapter and the power receiving means is a rechargeable battery which may be located in the mastoid.

Usually, the external audio signal unit will comprise at least one microphone for generating the input audio signals to the audio signal processing unit.

Further preferred embodiments are defined in the sub-claims.

Hereinafter examples of the invention will be illustrated by reference to the attached drawings, wherein:

FIG. 1 is a schematic view of an example of a partially implantable hearing aid comprising an electro-mechanical actuator.

Figure 1:
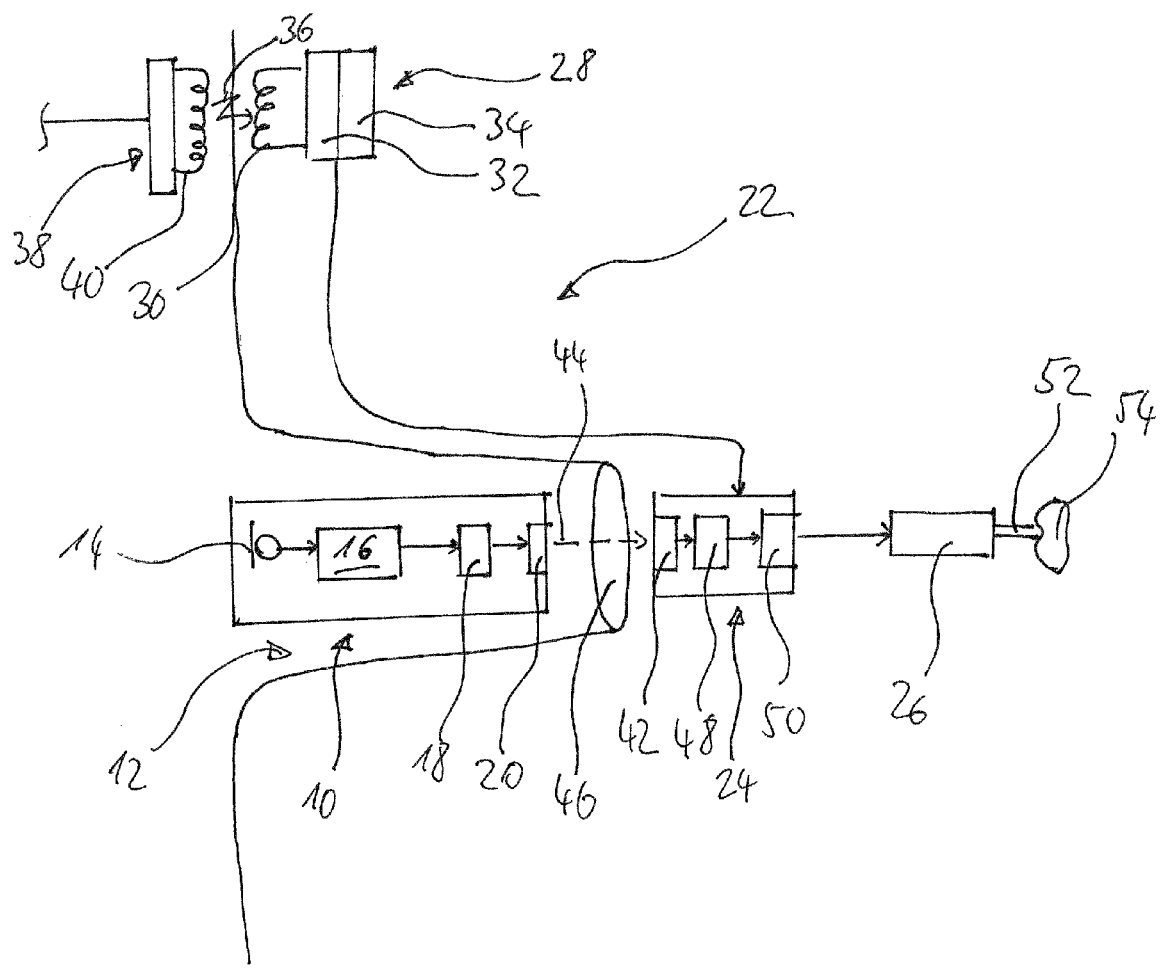
FIG. 1 is a schematic view of an example of a partially implantable hearing aid according to the invention comprising an electromechanical actuator.

The system comprises an external audio signal unit 10, which is designed as a modified CIC hearing aid and which is to be worn in the user's ear canal 12. The external unit 10 comprises a microphone arrangement 14, an audio signal processing unit 16, a transmitter circuit 18 and a LED (Light Emitting Diode) 20. The microphone arrangement 14 may comprises at least two spaced-apart microphones (not shown) in order to provide for acoustic beam forming capability. The audio signal processing unit 16 processes the audio signals provided by the microphone arrangement 14 and supplies the processed audio signals to a transmitter circuit 18 which drives the LED 20. The external unit 10 also comprises a battery (not shown) which may be rechargeable. The audio signal processing unit 16 preferably is implemented by an ultra-low power hearing instrument DSP (Digital Signal Processor) of the type which is also used in electro-acoustic CIC hearing aids. Thus, the external part 10 is quite similar to a CIC hearing aid, with the loudspeaker being replaced by the transmitter circuit 18 and the LED 20. Thereby, all signal processing algorithms and procedure available in CIC hearing aids may be straightforwardly applied to the external unit 10, with only minor modifications due to the different output transducer being necessary.

The system also includes an implantable unit 22 comprising an implanted audio signal unit 24, an electro-mechanical actuator 26 and a power management unit 28.

The power management unit 28 comprises a power receiving coil 30, a power management circuitry 32 and a rechargeable battery 34. The battery 34 is charged via transcutaneous inductive power link 36 by an external charging adapter 38 comprising a power transmission coil 40 which transmits power to the power receiving coil 30 of the power management unit 28.

The implantable audio signal unit 24 is located in the middle-ear cavity close to the ear drum 46 and comprises a photo diode 42 as an optical receiver for light 44 which is emitted by the LED 20 and which passes through the ear drum 46, a decoder 48 for retrieving the audio signals from the received light 44 and a driver unit 50 for driving the actuator 26. The implantable audio signal unit 24 may be packaged in glass.

The actuator 26 is an electro-mechanical transducer which is coupled via a coupling element 52 to a middle-ear component 54, namely an ossicle or the cochlear wall. The actuator 26 may be designed, for example, as a floating mass transducer (FMT) fixed at one of the ossicles or a direct acoustic cochlear stimulator (DACS) directly acting on the cochlear wall, i.e. foot plate, oval window, round window or any artificial opening of the cochlea.

The rechargeable battery 34 of the power management unit 28 should be dimensioned for lasting at least a full day and it should be possible to recharge it within a few hours; charging must be feasible during normal operation of the hearing aid or at night. Preferably, the rechargeable battery 34 is designed in thin-film lithium technology.

The power management unit 28 serves as the power supply for the implantable audio signal unit 24 and the actuator 26.

According to a modified embodiment, the audio signal unit 10 may be designed as a modified BTE hearing aid wherein the LED 20 is located in the ear canal 12. In this case, the LED 20 is connected by wire to the external part of the BTE hearing aid in a manner similar to manner in which an ex-receiver is connected to a BTE hearing aid, with the external part which is located behind the user's ear comprising the microphone arrangement 14, the audio signal processing unit 16 and the transmitter circuit 18. In other words, according to such embodiment, the ex-receiver of a conventional BTE hearing aid would be replaced by an optical audio signal transmitter comprising the LED 20.

Figure 2:
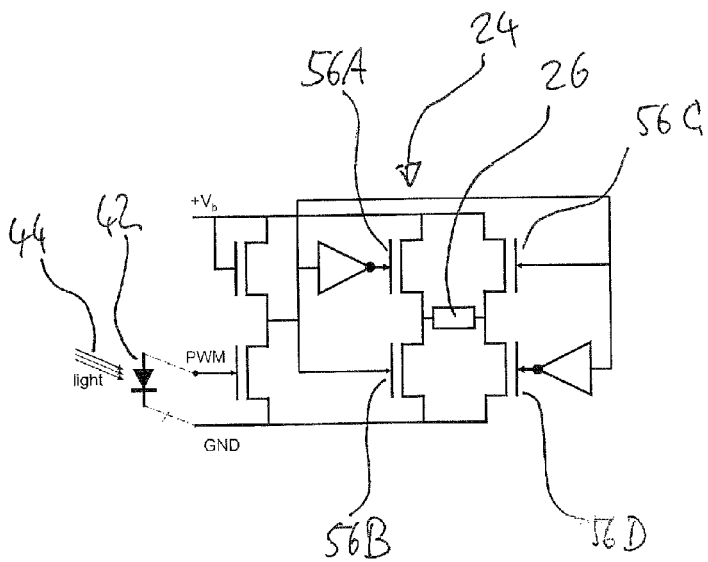
FIG. 2 is an example of a driver circuit for the actuator of the hearing aid of FIG. 1.

FIG. 2 shows an example of the circuitry of the implantable audio signal unit 24, wherein the photo diode 42 triggers a H-bridge comprising four switches 56A, 56B, 56C and 56D, which drives the actuator 26 as a floating load. The driving signal of a H-bridge usually is a pulse width modulated signal or a pulse density modulated signal, i.e. a purely digital pulse-train, the analogue-to-digital conversion is done by the low-pass characteristics of the actuator 26 itself. The decoder 48 is implemented as part of the H-bridge. Thus, an extremely simple design requiring only a couple of logic gates is realized.

Figure 3:
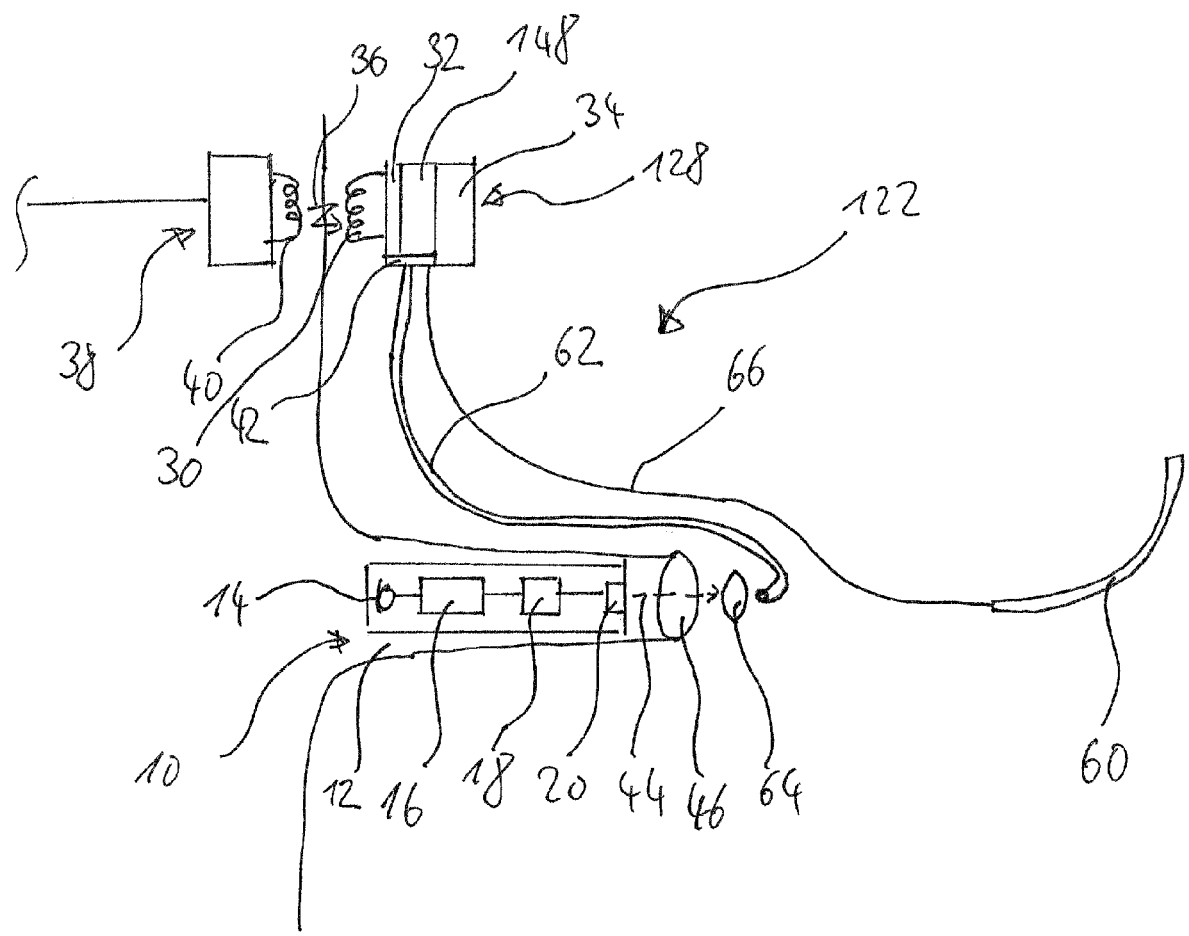
FIG. 3 is an example of a partially implantable hearing aid according to the invention comprising a CI.

FIG. 3 shows an alternative embodiment of the invention, wherein the actuator is a cochlear electrode 60. In this case, the power management unit 128 in addition to the power control 32, the power receiving coil 30 and the rechargeable battery 34 comprises a signal decoder/driver unit 148 and a photo diode 42. The photo diode 42 is integrated within the housing of the power management unit 128 and detects light supplied by an implanted optical fibre 62. Light 44 which is emitted by the LED 20 of the external audio signal unit 10 and which has passed through the ear drum 46 is collected by a lens 64 and is coupled into one end of the optical fibre 62 by which it is guided to the photo diode 42. The decoder/driver unit 148 supplies electrical stimulation signals to the cochlear electrode 60 via a wire 66. The lens 64 is located in the middle ear cavity close to the ear drum 46, whereas the unit 128 is implanted in the mastoid.

According to a modified embodiment, which is not shown in FIG. 3, the photo diode 42 may be located in the middle-ear cavity close to the ear drum 46 in the manner shown in FIG. 1, with the output signal of the photo diode being supplied by wire to the unit 128.

The invention claimed is:

1. A partially implantable hearing aid comprising:
   an external audio signal unit to be worn at least in part in a user's ear canal,
   an implantable unit, and
   an external means for transmitting power transcutaneously to the implantable unit via an inductive link,
   wherein the external audio signal unit comprises an audio signal processing means for producing processed audio signals from input audio signals and means for transmitting the processed audio signals via an optical link through an ear drum to an optical receiver of the implantable unit, and
   wherein the implantable unit comprises an actuator for stimulating a user's hearing, a power receiving means and a driver unit for transforming received audio signals into an input signal to the actuator.

2. The hearing aid of claim 1, wherein the external means for transmitting power is a charging adapter and wherein the power receiving means comprises a rechargeable battery.

3. The hearing aid of claim 2, wherein the rechargeable battery is for being located in a mastoid.

4. The hearing aid of claim 1, wherein the external audio signal unit comprises at least one microphone for generating the input audio signals.

5. The hearing aid of claim 1, wherein the external audio signal unit is designed as a CIC device.

6. The hearing aid of claim 1, wherein the means for transmitting the processed audio signals comprises a LED to be located in the user's ear canal.

7. The hearing aid of claim 1, wherein the optical receiver comprises a photo diode to be located in a middle ear.

8. The hearing aid of claim 1, wherein the actuator is a cochlear electrode.

9. The hearing aid of claim 8, wherein the optical receiver comprises:
   a photo diode,
   a light collecting means located in a middle ear for collecting light received from the external audio signal unit and
   an optical fiber for passing light from the light collecting means to the photo diode.

10. The hearing aid of claim 9, wherein the photo diode is for being located in a mastoid.

11. The hearing aid of claim 8, wherein the driver unit is for being located in a mastoid.

12. The hearing aid of claim 11, wherein the driver unit is located in a housing common with the rechargeable battery.

13. The hearing aid of claim 1, wherein the actuator is an electromechanical transducer to be coupled to an ossicle or to a cochlear wall.

14. The hearing aid of claim 13, wherein the driver unit is for being located in a middle ear.

15. The hearing aid of claim 13, wherein the driver unit is designed as a H-bridge circuit triggered by a photo diode.

16. The hearing aid of claim 15, wherein the photo diode and the driver unit are packaged in glass.

* * * * *